(12) United States Patent
Matias

(10) Patent No.: US 10,010,641 B2
(45) Date of Patent: Jul. 3, 2018

(54) DISPENSING UNIT

(71) Applicant: Carlos Jose Duarte Matias, Lisbon (PT)

(72) Inventor: Carlos Jose Duarte Matias, Lisbon (PT)

( * ) Notice: Subject to any disclaimer, the term of this patent is extended or adjusted under 35 U.S.C. 154(b) by 148 days.

(21) Appl. No.: 14/769,394

(22) PCT Filed: Apr. 21, 2014

(86) PCT No.: PCT/IB2014/001217
§ 371 (c)(1),
(2) Date: Aug. 20, 2015

(87) PCT Pub. No.: WO2014/135990
PCT Pub. Date: Sep. 12, 2014

(65) Prior Publication Data
US 2016/0000958 A1     Jan. 7, 2016

Related U.S. Application Data

(60) Provisional application No. 61/767,083, filed on Feb. 20, 2013.

(51) Int. Cl.
| | | |
|---|---|---|
| *A61L 9/12* | (2006.01) | |
| *A01M 1/20* | (2006.01) | |
| *A01M 29/12* | (2011.01) | |
| *A61M 21/02* | (2006.01) | |
| *A61M 21/00* | (2006.01) | |

(52) U.S. Cl.
CPC .............. *A61L 9/12* (2013.01); *A01M 1/2027* (2013.01); *A01M 1/2061* (2013.01); *A01M 29/12* (2013.01); *A61M 21/02* (2013.01); *A61L 2209/11* (2013.01); *A61L 2209/12* (2013.01); *A61M 2021/0016* (2013.01); *A61M 2021/0044* (2013.01)

(58) Field of Classification Search
CPC .............................. A61L 9/12; A01M 1/2027
USPC ......................................................... 422/123
See application file for complete search history.

(56) References Cited

U.S. PATENT DOCUMENTS

| | | | |
|---|---|---|---|
| 5,014,913 A * | 5/1991 | Hoyt ......................... | A61L 9/12 239/45 |
| 5,437,410 A | 8/1995 | Babasade | |
| 5,520,202 A * | 5/1996 | Arbree ................. | A45C 11/008 132/148 |
| 5,874,050 A | 2/1999 | Matias | |
| 6,412,640 B1 * | 7/2002 | Destanque ............. | A45D 33/28 132/297 |

(Continued)

*Primary Examiner* — Kevin Joyner
*Assistant Examiner* — Holly M Mull
(74) *Attorney, Agent, or Firm* — Ware, Fressola, Maguire & Barber LLP

(57) ABSTRACT

A dispensing unit has a base with two or more upwardly projecting side panels hingedly attached thereto. The sides have upper ends which pivot inwardly to a closed position, and outwardly to an open position. One or more removable dispensable compound containers are locatable within the unit, positioned adjacent a relative movable side panel. Each side has a capping projection that is located over and caps the container when the side panel is in a closed position, and which uncap the container when in the open position. When the sides are pivoted outwardly, they permit dispensing of the dispensable compound located in each container.

12 Claims, 8 Drawing Sheets

(56) References Cited

U.S. PATENT DOCUMENTS

| | | |
|---|---|---|
| 6,729,552 B1 | 5/2004 | McEwen et al. |
| 6,742,930 B2 | 6/2004 | Matias |
| 6,966,500 B1* | 11/2005 | Kelley ................ A01M 31/008 |
| | | 239/34 |
| 7,332,140 B2 | 2/2008 | Matias |
| 7,520,635 B2 | 4/2009 | Wolf et al. |
| 7,717,258 B2 | 5/2010 | Stephens |
| 7,997,565 B1 | 8/2011 | Chan |
| 2005/0145711 A1* | 7/2005 | Blondeau .................. A61L 9/12 |
| | | 239/60 |
| 2005/0285538 A1 | 12/2005 | Jaworski et al. |
| 2008/0130266 A1* | 6/2008 | DeWitt ..................... A61L 9/03 |
| | | 362/96 |
| 2011/0049266 A1 | 3/2011 | Jorgensen |

* cited by examiner

DISPENSING UNIT

CROSS REFERENCE TO RELATED APPLICATIONS

This application claims priority in U.S. Provisional Patent Application No. 61/767,083 filed Feb. 20, 2013.

BACKGROUND

There have been a number of attempts to improve the ambience in an interior space, such as by providing various types of dispensers for releasing fragrances, for altering lighting to be more pleasing or to enhance mood.

Lighting has been combined with devices such as air fresheners or air deodorizers, which may also include the release of compounds such as fragrances and essential oils. Other products which combine lighting effects with fragrance release may include scented candles, plug-in fragrance dispensers, and the like. While these devices may foster a more pleasant environment, there are a number of drawbacks, such as the need to rely on a flame, or uneven scent distribution, too strong initially, running to too weak as the volatiles are removed. Another is that they generally come with a fixed fragrance, and do not allow a user to switch easily to another fragrance. Also, plug-in dispensers require that an outlet be used with the fragrance released often in a less accessible location, with the amount of lighting being quite limited, typically being only used as a night light.

Some air sterilizing devices are known, for example as described in U.S. Pat. Nos. 7,332,140 and 5,874,050, both of which were invented by the applicant of the present application. In these devices, air flows by convention through heated capillaries which destroy microorganisms at high temperatures. While such air sterilizers are effective in treating contaminated air, it would be desirable to combine features supporting air sterilization with aspects of aromatherapy, or possibly for use in dispensing insecticides or insect repellants in country infested by mosquitos, and also chromo therapy, and to perform at least one of those extra functions in a single device.

There is also a need to provide remote control of the dispensing of substances within the home, while the home is not occupied via remote control, particularly in countries infested by mosquito transmitting diseases such as "dengue". It would be advantageous to provide a remotely operated system to release insecticides to kill mosquitoes before entering a specific room in the house or even before entering the house from outside with the advantage of safely entering the ambiance without the inconvenience of inhaling the insecticides. This provides the benefit of knowing before hand that an area is relatively free of mosquitoes, and this may be accomplished preferably with a dispensing device that can be operated by remote control, for instance, using WIFI.

SUMMARY OF THE INVENTION

It is an object of the present invention to provide a device that is effective in sterilizing and/or cleaning the air, and additionally supports the incorporation of dispensable compounds such as fragrances, repellants and/or insecticides in the air exiting from the device which may optionally include an air filtration unit.

It is another object to preferably incorporate light generating elements in the air sterilizing and/or purification unit which can generate a range of colors to support chromo therapy, and generally improve the ambient environment.

It is yet another object of the present invention to provide an air sterilizing and/or air filtration unit which has independent switching mechanisms for activating light generation and/or dispensing compounds such as but not limited to aromatic fragrances, insecticides or insect repellants. In one embodiment, combinations of these can be dispensed, such as two fragrances, or one fragrance and one insect repellent, etc., with the device incorporating operating elements which enable to user to dispense one or more compounds together or independently of each other.

These and other object of the present invention are achieved by at least one a dispensing unit having a base, a plurality of upwardly projecting sides hingedly attached thereto, the sides having upper ends which pivot inwardly to a closed position, and outwardly to an open position, at least one removable aromatherapy container locatable within the unit, the at least one container positioned adjacent a relative movable side, the movable side having a capping member that is located over and caps the container when the sides are in a closed position, and which uncap the container when in the open position, such that when the sides are pivoted outwardly, they permit dispensing of a dispensable compound, such as an aromatherapy agent and/or insecticide, disposed in each container.

In one embodiment of the invention, the aromatherapy dispensing unit has a central activator which holds the at least one removable containers for a dispensable compound such as but not limited to essential oils, fragrances, insecticides, repellants, medical substances or the like, adjacent a top opening of the unit. The central activator is reciprocally movable and linked to the pivotable sides such that when the sides are in the inward closed position, the central activator is in an upper position, with the fragrance container capped, and that when pushed downwardly, the sides pivot outwardly, uncapping the container to permit release of the fragrance, as well as to allow the removable container to be removed, filled with a selected fragrance agent, and then replaced in the unit. Pivoting the sides inwardly to close the container displaces the central activator upwardly, so as to permit the container to be capped.

Optionally, the central activator further contains at least one light source, preferably dimmer controlled. Other components such as a fan for drawing air into the device and directing the air upwardly past the fragrance container, or powered air sterilizer components, can also be turned on when the central activator is pushed downwardly, and turned off when the sides are pivoted into the closed position, though independent controls for these optional components could also be used.

BRIEF DESCRIPTION OF THE DRAWINGS

For a fuller understanding of the invention, reference is made to the following description of one embodiment taken in connection with the accompanying drawings, in which.

DETAILED DESCRIPTION OF THE INVENTION

Figure 1:
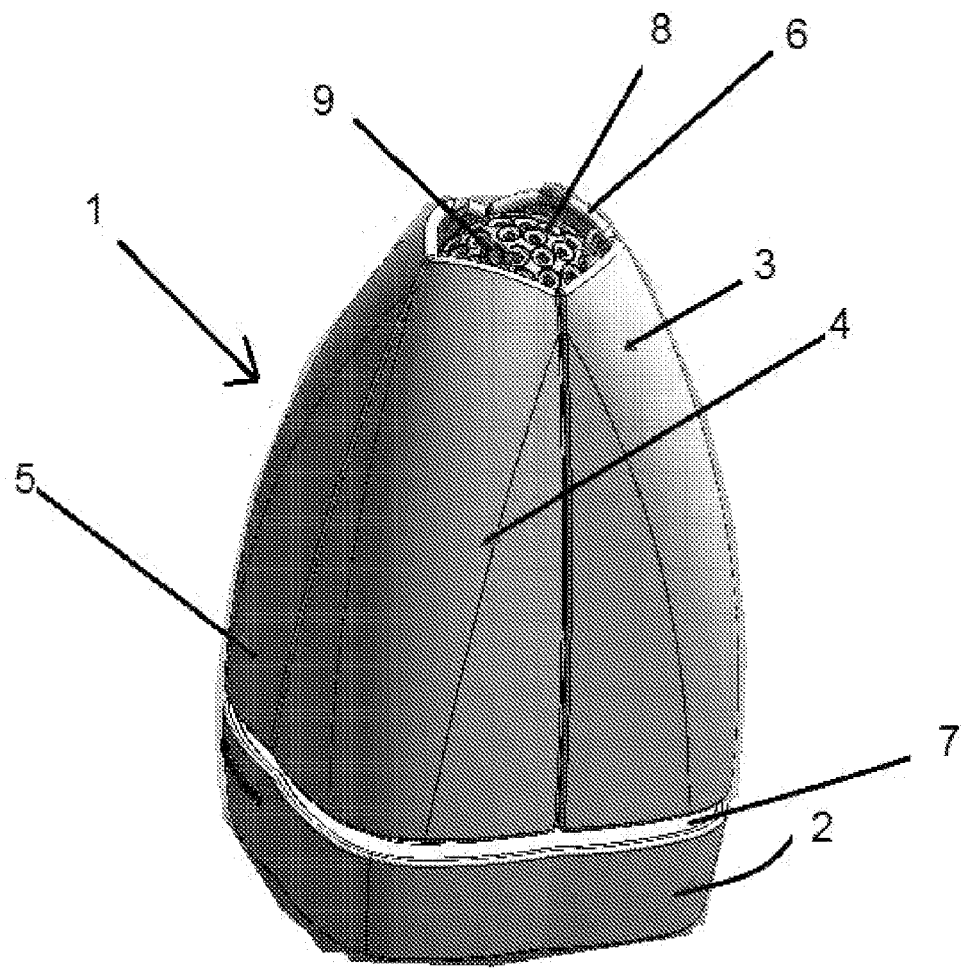
FIG. 1 is a perspective view of one embodiment of the aromatherapy dispensing unit of the present invention, incorporated with an air sterilizer device with the side panels shown in a closed position.

Referring to FIG. 1, one embodiment of an aromatherapy dispensing unit 1 has a generally square base 2 spaced away from four side panels 3, 4, 5 and 6 which are similar to flower petals, being pivoted outwardly to simulate the opening of a flower. Of course, four sides is merely one embodiment of the invention, and two or more sides can also be used and the invention is not limited by the number of side panels. A space 7 between the base and the side panels forms an air entry area. A central globe 8 has holes 9 which provide air outlets, the globe emerging between top edges of the side panels, so as to resemble the central portion of a flower. The central globe may be transparent or have light transmitting openings so that light when present can pass through the globe to create various lighting effects.

In this embodiment, each of the movable panels forming the petals is wider at a bottom thereof and tapers towards the top, with each side or petal hinged so that the tapered top part can pivot inwardly and outwardly, creating a greater open space at the top when opened than at the bottoms, to allow dispensable compounds, such as fragrances, to be dispensed when present and/or to allow more light, when present, to exit the unit.

Figure 2:
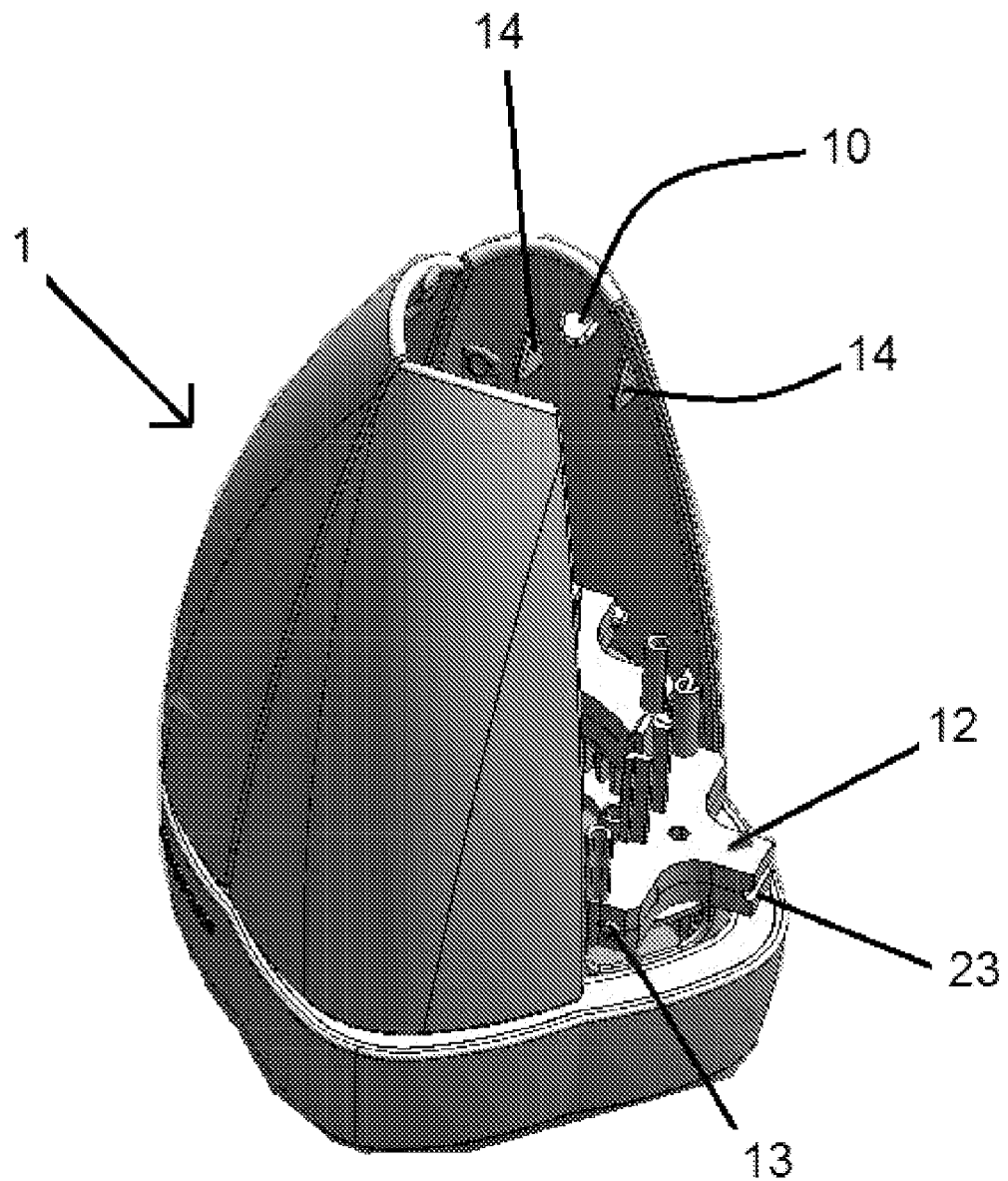
FIG. 2 is a partial sectioned view of one embodiment of the unit, with one side panel removed to illustrate portions of the operating mechanisms.

FIG. 2 shows the unit 1 with one side panel and the central activator removed, for ease in illustrating the operation of the unit. Each side panel has an inwardly extending projection 10 towards the upper end, located so as to act as a closure for a removable container 11 (See FIG. 3) that is removably housed in the central activator and filled with a dispensable compound, such as a fragrance agent. A panel support 12 has a pair of pivot pins 13 which permit the panels to pivot inwardly and outwardly, as will be discussed further below. Each side panel also includes a pair of inwardly projecting sloped tabs 14 which guide the panel for movement inwardly or outwardly in coordination with upward or downward movement of the central globe 8, as will also be discussed further below.

The term "Dispensable Compound" is used herein to define ingredients suitable for inclusion in the removable container for evaporative dispensing, including but not limited to, a fragrance, an air freshener, a deodorizer, an odor eliminator, a malodor counteractant, an insecticide, an insect repellant, a medicinal substance, an aromatherapy substance, a disinfectant, a sanitizer, a mood enhancer, or the like, and combinations thereof, in liquid, oil or gel form, these ingredients generally comprising one or more volatile organic compounds. In accordance with the dispenser of the present invention, such a dispensable compound is placed in the receptacle and via natural convention, or by heating or other means, air flows by the receptacle, with evaporation of the dispensable compound into the air thereby dispensing the compound. While simply exposing the dispensable compound to the air results in evaporation, various methods can be used to increase dispersion. For example, if placed above an air sterilization unit, heated air produced during the sterilization will pass by the removable receptacle and readily acquire the dispensable compound for dispensing the compound into the adjacent area, such as an interior room. Suitable dispensable compounds for use with the dispenser or the applicants' invention will be apparent to those skilled in the art.

Figure 3:
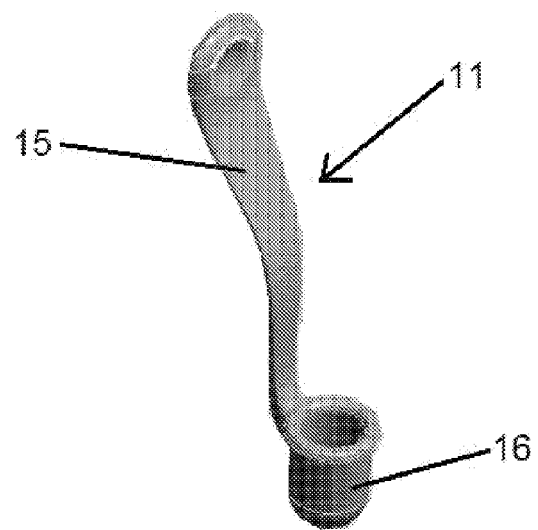
FIG. 3 is a view of one embodiment of a removable dispensable compound container usable with the present invention.

With reference to FIG. 3, the removable container 11 is shown which has a handle 15 and a cup 16 for holding the dispensable compound therein. The removable containers can be either reusable by refilling with a dispensable compound, or may be disposable after the compound is consumed, purchased in a pre-packaged form with a lid that is removable before placement in the unit. The size of the opening into the cup corresponds to a size of the projection 10 which is position so that when the panels are pivoted inwardly into a closed position, a cup of the removable container associated with that particular panel is capped, and such that when the side panels pivot outwardly, simulating the opening of a flower, the projection 10 is displaced away from the cup so that the dispensable agent is released. In this embodiment, with four petals, up to four removable containers may be contained in the unit. It should be noted that in one embodiment, all the panels can be opened and closed simultaneously, while in another embodiment, the panels can be opened independently of each other. Preferably, the setting as to which panels open is user configurable.

Figure 4:
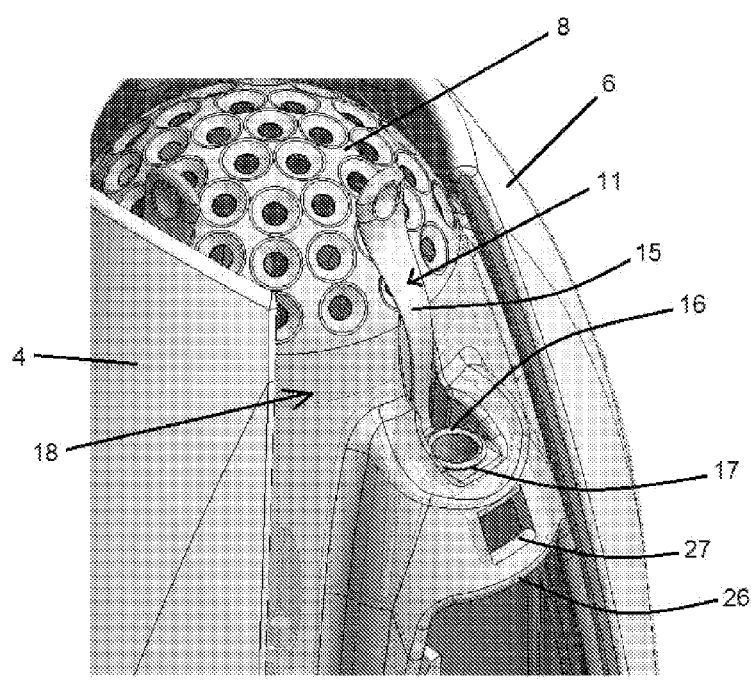
FIG. 4 is a sectional view showing one embodiment of the removable container as mounted to the central activator.
Figure 5:
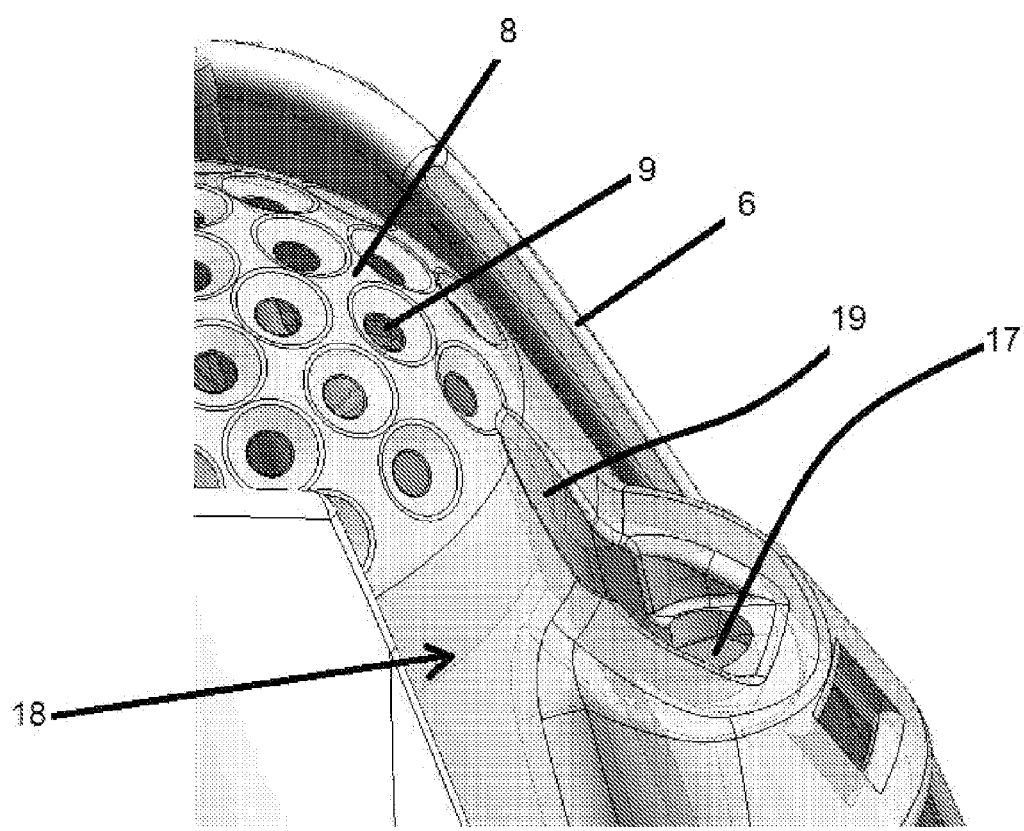
FIG. 5 is an enlarged view showing the receptacle which receives the container.

Referring to FIG. 4, the removable container 11 is shown located within the unit 1. The cup 16 resides within a receptacle 17 that is formed integrally with a central activator 18 which includes the globe 8. The handle 15 extends upwardly so as to ease loading and unloading from the receptacle. This allows the container 11 to be easily removed and filled with a selected dispensable compound such as an aromatherapy agent or to be replaced with a single use disposable type container. The containers 11 are located along each side of the globe 8, facing a respective side panel and in alignment with a respective projection 10 for capping and uncapping the cup 16. The projection 10 also holds the container in position, when the side panels are in the closed position, each side panel being movable relative thereto for capping or uncapping the container. FIG. 5 is a view of the activator 18 without the removable container 11, to better illustrate the receptacle 17 and a handle support channel 19 which together snugly receive the container 11 therein.

Figure 6:
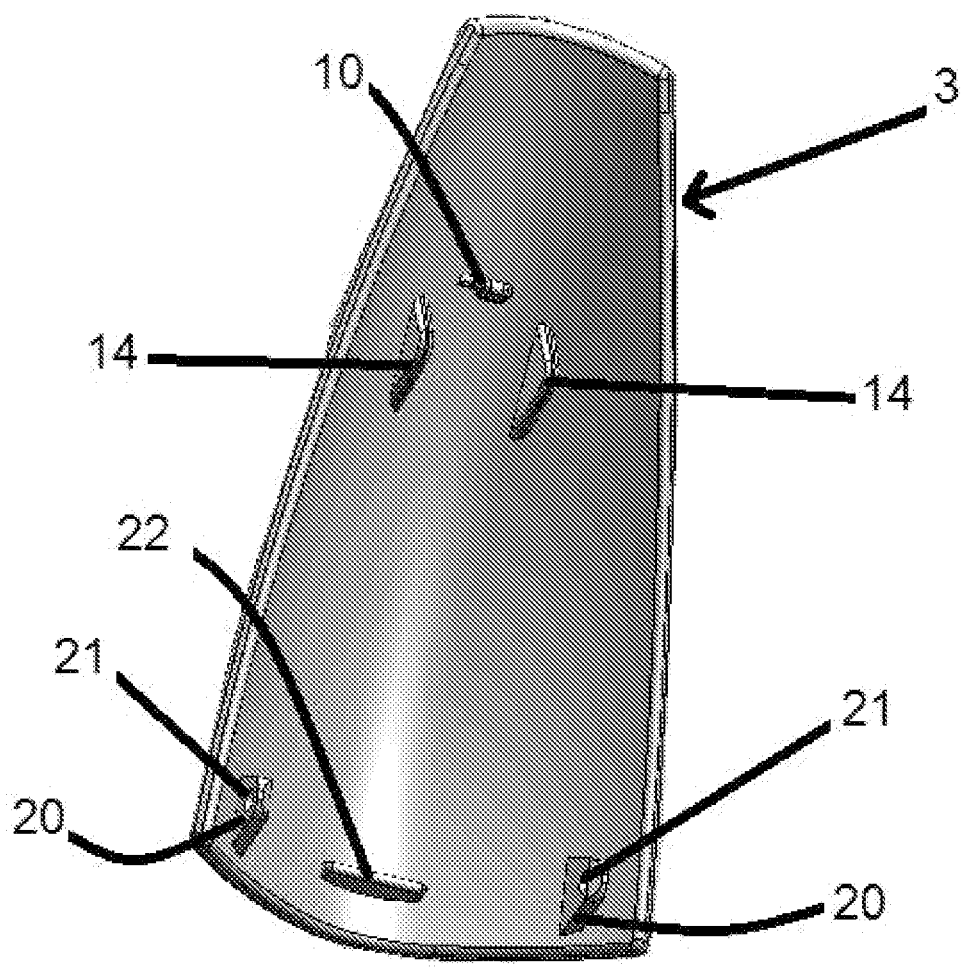
FIG. 6 is a view showing the structures incorporated on an interior surface of a side panel.

Referring to FIG. 6, the side panel 3 has the projection 10 disposed centrally relative to the guide tabs 14. A pair of lower pivot connectors 20 has openings 21 for mating with and receiving the pivot pins 13 located on the panel support 12. A fin 22 is also provided which is receivable within a recess 23 located in the panel support 12. (See FIG. 2) The fin mating with the recess provides a stop for the side panel when pivoted into the open position. While a pivoting connection is disclosed in this embodiment, there are other ways in which the movable side panel can move from an open position where the dispensable compound in the receptacle is exposed to the environment and a closed position where the receptacle is capped, that is, to a closed position. For example, structures can be provides for moving the movable panel upwardly and downwardly to cap and uncap the receptacle cup, or the movable panel can slide sideways to cap and uncap the receptacle cup, and the invention is not limited to the hinged embodiment illustrated.

Figure 7:
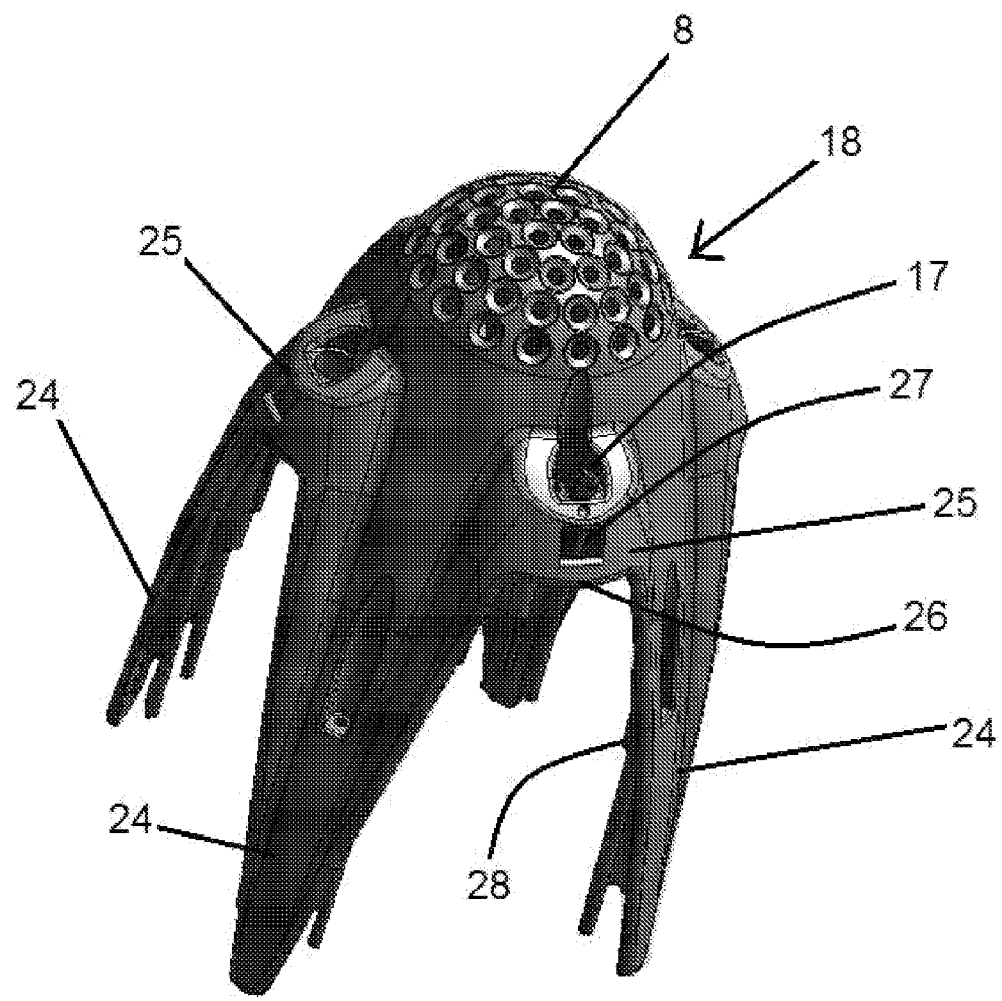
FIG. 7 is a perspective view of the central activator including LED receptacles, as removed from the unit for ease of illustration.

Referring to FIG. 7, the central activator 18 is shown removed from the unit 1 for ease in illustration. The central activator 18 has four legs 24 which extend downwardly from the central globe 8, between pairs of which are located one or more container supports 25 which each include a respective receptacle 17 for the removable container 11 as previously described. Each container support 25 has a forward guide lip 26 and a locking chamber 27 which will be described further below. Each leg 24 has two tubular channels 28 which preferably receive rgb LEDs to provide a mixture of color generated by the LED's according to a user configurable program for creating lighting effects that act as generally pleasing to the user or for supporting chromotherapy. The central globe has a plurality of opening which are used to permit air flow therethrough. Preferably either the globe supports the LED light sources or these can be mounted in other parts of the unit, and operated in coordination with the dispensing function.

Figure 8:
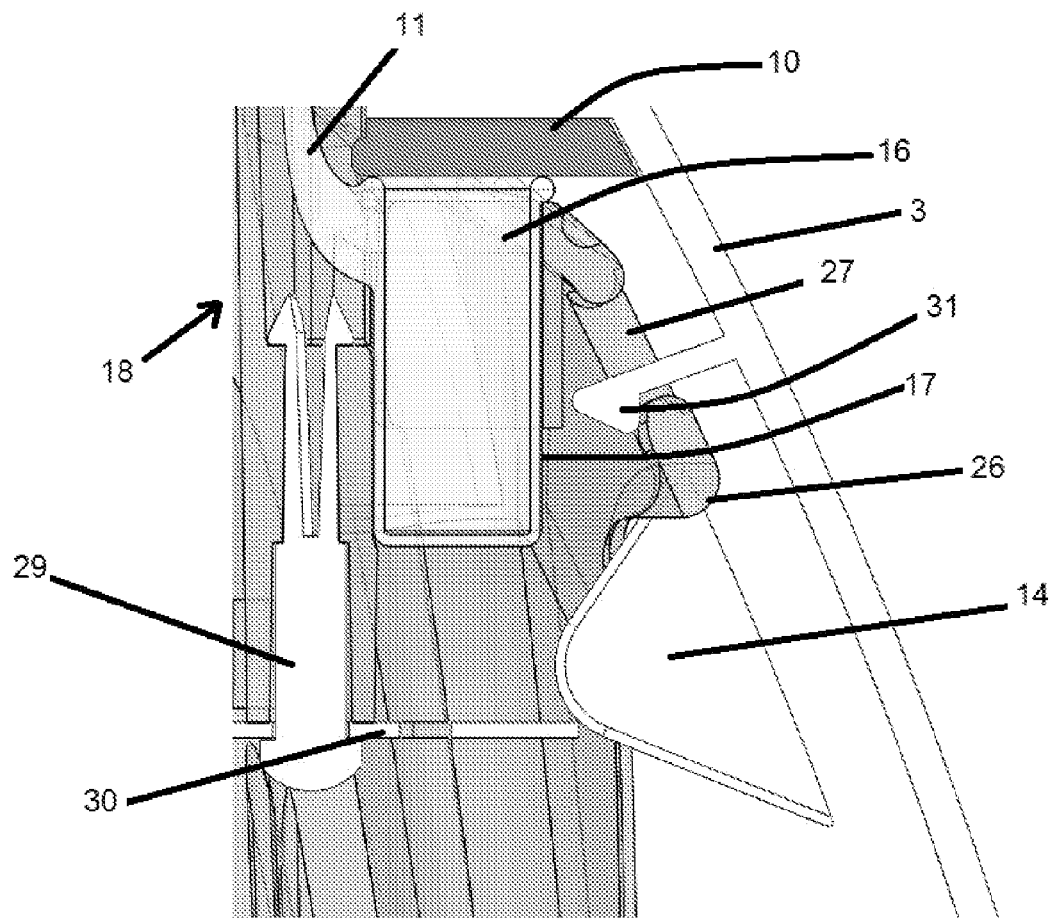
FIG. 8 is an enlarged cross sectional view of a side panel engaged with the central activator, with the side panel in the closed position and the removable container capped; and, FIG. 9a is a cross sectional view showing the side panel in the closed position with the central activator in its uppermost position; and, FIG. 9b is a cross sectional view of the side panel in the open position with the central activator pushed down to a lowermost position.

Referring to FIG. 8, an enlarged partial cross sectional view of the unit shows the removable container 11 mounted in the receptacle 17 with the projection 10 received over and covering the opening in the cup 16. Also shown is the engagement of the forward guide lip 26 with the guide tabs 14. Note the location of the engagement of the forward guide lip on the sloped surface of the guide tab 14. The fastener 29 is shown connecting the central activator 18 to the reciprocally movable planar support 30. In this embodiment a locking detent 31 extends from the side panel which is received within the locking chamber 27, to, in essence, provide a snap fit when the panels are in the closed position.

Figure 9A:
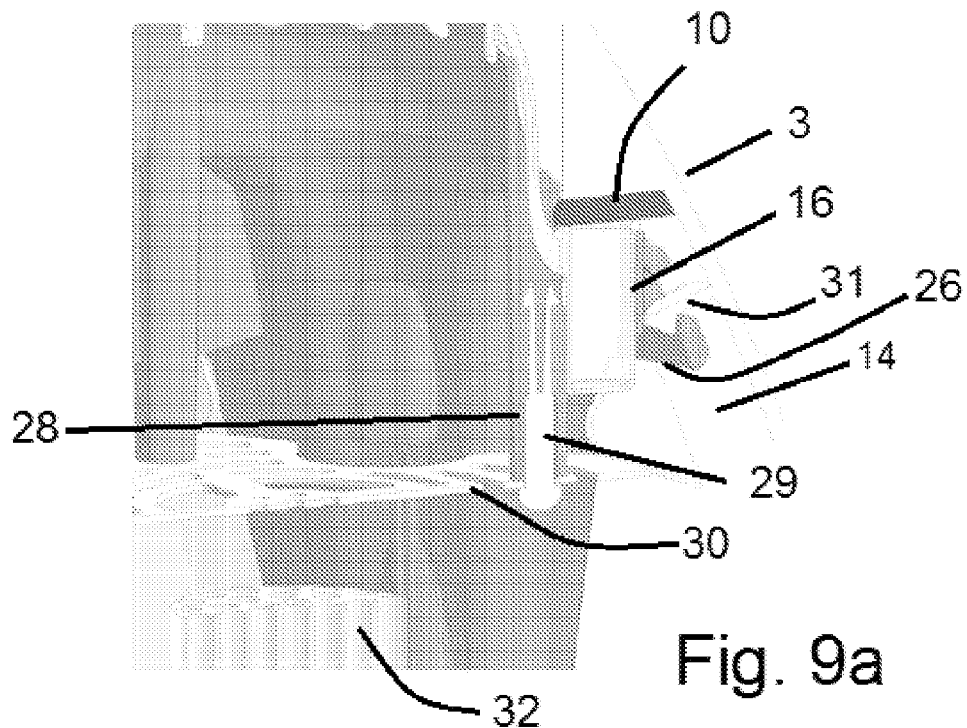
Figure 9B:
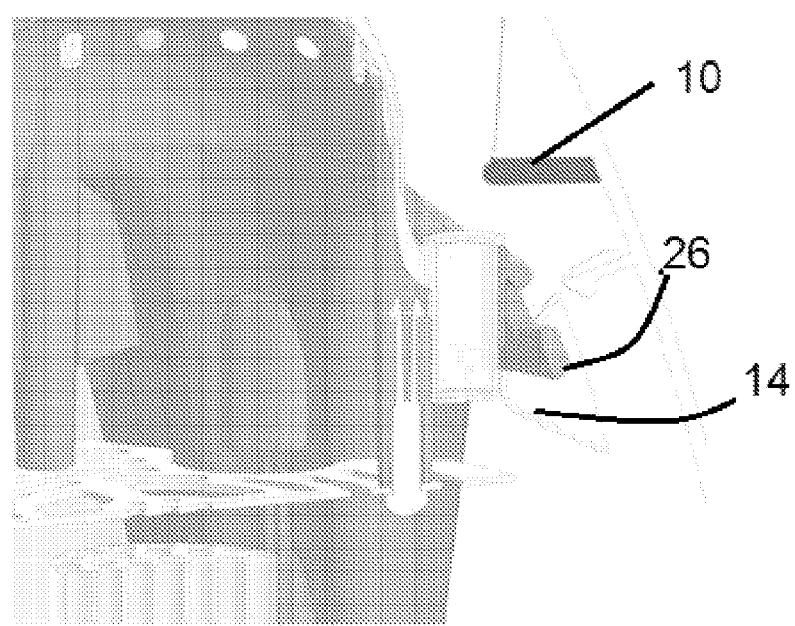

Referring to FIGS. 9a and 9b, one method of opening and closing the panels is shown. In FIG. 9a, the cup 16 is capped by the projection 10 and the forward lip is located at an upper part of the sloped surface of the guide tab 14. The locking detent is also received in the locking chamber. In operation, the globe in this position is at its' top most position, the cup is caped and no dispensable compound is being released. To operate the unit, a user would push down on the globe, displacing the central activator downwardly which causes the forward lip, as it moves downwardly, to displace the side panel outwardly, into the position shown in FIG. 9b. Here it is seen how the projection 10 is displaced away from the cup, allowing a dispensable compound to be dispensed.

Displacement of the globe and central activator also closes electrical contacts to turn on any electrically powered components, if present. For example, lighting, a fan for driving air through the unit, or other devices, could all be activated by a simple push down of the central activator. Conversely, a user can press the side panels inwardly to drive the central activator back to its' uppermost position, breaking the contacts to turn off the powered elements of the unit while simultaneously capping the cup holding any remaining dispensable compound therein. With the side panels in the closed position, the central activator which preferably includes a lighting transmitting device, is visible, with the light turned on when the side panels are pivoted outwardly, not only to dispense the dispensable compound such as a fragrancing agent, but the illuminated globe will irradiate light through the openings formed by the side panels as well.

It should be understood that various electrical, electronic and computing devices could be housed within the unit. For example, a fan or other air moving device may be incorporated into the base so as intake room air and discharge the air within the unit so it flows upwardly by the containers, so as to enhance the dispensing of the aromatherapy agent when the sides are in the opened position. In addition, various controls and communication devices could also be housed therein. In particular, while a simple lip and tab system is shown for opening and closing the side panels, a substitute would be micro devices associated with each individual panel, activatable in response to a control signal for opening and closing the panels individually, possibly via wireless remote control, or following a user configurable program stored on a microprocessor incorporated with the device. For example, a user may load each of the four illustrated receptacles with different dispensable compounds, such as three different fragrancing agents and one insect repellant, and then program the device to operate and open different receptacles at different times or according to a programmed sequence. The computing device or microprocessor could also include a user configurable lighting program, for example, delivering different colored lighting or dimming control in association with particular agents as they are released, or provide controllable lighting independently of the opening and closing of the side panels. Additionally, communications devices may be incorporated for remote control via IR, Bluetooth, etc., or enable access to a wireless network for internet control. One or all of these features can be incorporated into the dispensing unit of the applicants' invention.

While preferred embodiments of the invention have been shown and described, it will be understood that various changes or modification could be made without varying from the spirit or scope of the present invention. For example, one possibility contemplated by the inventor would be to remotely dispense an insecticide or the like followed by a fragrance, coming from two different receptacle containers, being opened and closed in programmable sequence or via remote or internet control, or in accordance with a pre-set timed program. Similarly, the receptacles can hold dispensable compounds suitable for medical use, where the receptacles with the same or different medicines are timely opened in accordance with a pre-set program.

The invention claimed is:

1. A dispensing unit for dispensing a dispensable compound comprising:
   a base,
   a plurality of side panels movably attached thereto, at least one side panel having an upper end which moves from a closed position to an open position,
   at least one removable dispensable compound container locatable within the unit, each removable dispensable compound container of the at least one removable dispensable compound container positioned adjacent only a corresponding one side panel of the at least one movable side panel, the at least one movable side panel having a capping member that is located over and caps the corresponding container when the side panel is in the closed position, and that uncaps the corresponding container when the at least one movable side panel is moved into the open position, such that when the corresponding one side panel is moved outwardly, the dispensable compound disposed in the corresponding container is exposed to the atmosphere, and
   a central activator within the dispensing unit, engaged with the plurality of side panels such that when the central activator is manually moved toward the base, a resultant displacement of the central activator within the dispensing unit moves the at least one side panel to the open position, and such that subsequent manual movement of the at least one side panel from the open position to the closed position reverses the displacement of the central activator within the dispensing unit.

2. A dispensing unit for dispensing a dispensable compound comprising:
a base;
a plurality of side panels movably attached thereto, at least one side panel having an upper end which moves from a closed position to an open position;
at least one removable dispensable compound container locatable within the unit, each removable dispensable compound container of the at least one removable dispensable compound container positioned adjacent only a corresponding one side panel of the at least one movable side panel, the at least one movable side panel having a capping member that is located over and caps the corresponding container when the side panel is in the closed position, and that uncaps the corresponding container when the at least one movable side panel is moved into the open position, such that when the corresponding one side panel is moved outwardly, the dispensable compound disposed in the corresponding container is exposed to the atmosphere; and
a central activator, engaged with the side panels such that displacing the central activator moves the at least one side panel to the open position, and moving the at least one side panel to the closed position reverses the displacement of the central activator, wherein the central activator has an illuminable globe on an upper end thereof.

3. A dispensing unit for dispensing a dispensable compound comprising:
a base;
a plurality of side panels movably attached thereto, at least one side panel having an upper end which moves from a closed position to an open position;
at least one removable dispensable compound container locatable within the unit, each removable dispensable compound container of the at least one removable dispensable compound container positioned adjacent only a corresponding one side panel of the at least one movable side panel, the at least one movable side panel having a capping member that is located over and caps the corresponding container when the side panel is in the closed position, and that uncaps the corresponding container when the at least one movable side panel is moved into the open position, such that when the corresponding one side panel is moved outwardly, the dispensable compound disposed in the corresponding container is exposed to the atmosphere; and
an air inlet located between the base and a bottom of the at least one side panel, air flow passing by the at least one side panel and at least one receptacle when the at least one side panel is in the open position.

4. The dispensing unit of claim 3 further comprising a central activator, engaged with the side panels such that displacing the central activator moves the at least one side panel to the open position, and moving the at least one side panel to the closed position reverses the displacement of the central activator.

5. The dispensing unit of claim 3 wherein the dispensable compound is selected from the group consisting of essential oils, fragrances, medical substances, insecticides, insect repellent and combinations.

6. The dispensing unit of claim 3 wherein the at least one movable side panel is hingedly attached to the base at a lower portion thereof, the at least one side panel being pivotable inwardly and outwardly between the closed position and the open position.

7. The dispensing unit of claim 3 wherein the at least one movable panel is adapted to move upwardly and downwardly between the open and closed positions.

8. The dispensing unit of claim 3 wherein the at least one movable panel is adapted to move sideways between the open and closed positions.

9. A dispensing unit for dispensing a dispensable compound comprising:
a base;
a plurality of side panels movably attached thereto, at least one side panel having an upper end which moves from a closed position to an open position;
at least one removable dispensable compound container locatable within the unit, each removable dispensable compound container of the at least one removable dispensable compound container positioned adjacent only a corresponding one side panel of the at least one movable side panel, the at least one movable side panel having a capping member that is located over and caps the corresponding container when the side panel is in the closed position, and that uncaps the corresponding container when the at least one movable side panel is moved into the open position, such that when the corresponding one side panel is moved outwardly, the dispensable compound disposed in the corresponding container is exposed to the atmosphere; and
a light source for generating light which is projected through a top of the unit and through an opening formed when the at least one side panel is in the open position.

10. A dispensing unit for dispensing a dispensable compound comprising:
a base,
a plurality of side panels movably attached thereto, at least one side panel having an upper end which moves from a closed position to an open position,
at least one removable dispensable compound container locatable within the unit, the container positioned adjacent the at least one movable side panel, the at least one movable side panel having a capping member that is located over and caps the container when the side panel is in the closed position, and which uncap the container when the at least one movable side panel is moved into the open position, such that when the side panel is moved outwardly, the dispensable compound disposed in each container is exposed to the atmosphere, and
a central activator, engaged with the side panels such that displacing the central activator moves the at least one side panel to the open position, and moving the at least one side panel to the closed position reverses the displacement of the central activator, wherein the central activator further comprises openings for permitting air flow therethrough or to receive lighting sources therein and combinations thereof.

11. A dispensing unit for dispensing a dispensable compound comprising:
a base,
a plurality of side panels movably attached thereto, at least one side panel having an upper end which moves from a closed position to an open position,
at least one removable dispensable compound container locatable within the unit, the container positioned adjacent the at least one movable side panel, the at least one movable side panel having a capping member that is located over and caps the container when the side panel is in the closed position, and which uncap the container when the at least one movable side panel is moved into the open position, such that when the side panel is moved outwardly, the dispensable compound disposed in each container is exposed to the atmosphere, and a central activator, engaged with the side panels such that displacing the central activator moves the at least one side panel to the open position, and moving the at least one side panel to the closed position reverses the displacement of the central activator, wherein the central activator has a receptacle support structure for receiving the removable container and a forward lip, the at least one side panel having a guide tab in engagement with the forward lip on a sloped surface thereof, such that moving the central activator downwardly pushes the at least one side panel outwardly to the open position, and pushing the at least one side panel to the closed position pushes the central activator to the uppermost position with respect to the base.

12. The dispensing unit of claim 11 wherein the side panel further comprises a locking detent, receptacle support structure including a locking chamber for receiving the locking detent when the side panel is in the closed position.

* * * * *